United States Patent [19]
Belikan et al.

[11] Patent Number: 5,095,908
[45] Date of Patent: Mar. 17, 1992

[54] APPARATUS FOR LOCATING OBJECTS WITHIN A BODY IN THREE DIMENSIONS AND FOR DESTROYING SUCH OBJECTS

[75] Inventors: Thomas Belikan; Werner Knauss, both of Knittlingen; Helmut Wurster, Oberderdingen, all of Fed. Rep. of Germany

[73] Assignee: Richard Wolf GmbH, Knittlingen, Fed. Rep. of Germany

[21] Appl. No.: 567,493

[22] Filed: Aug. 13, 1990

[30] Foreign Application Priority Data

Sep. 28, 1989 [DE] Fed. Rep. of Germany ....... 3932364

[51] Int. Cl.⁵ .............................................. A61B 17/22
[52] U.S. Cl. ............................ 128/660.03; 128/24 EL
[58] Field of Search ...................... 127/24 EL, 660.03; 606/127–128

[56] References Cited

U.S. PATENT DOCUMENTS

| | | | |
|---|---|---|---|
| 4,763,652 | 8/1988 | Brisson et al. ................. | 128/24 EL |
| 4,821,729 | 4/1989 | Makofski et al. .............. | 128/24 EL |
| 4,821,730 | 4/1989 | Wurster et al. ................ | 128/660.03 |
| 4,984,575 | 1/1991 | Uchiyama et al. ............. | 128/24 EL |

FOREIGN PATENT DOCUMENTS

| | | |
|---|---|---|
| 2722252C3 | 12/1979 | Fed. Rep. of Germany . |
| 3427001 | 2/1986 | Fed. Rep. of Germany . |
| 3743883 | 7/1988 | Fed. Rep. of Germany . |
| 2207247 | 1/1989 | United Kingdom ........... 128/24 EL |

OTHER PUBLICATIONS

Richard Wolf, GmbH, "Extracorporeal Piezoelectric Lithotripsy". Sep. 1988, Piezolith 2300.

*Primary Examiner*—Ruth S. Smith
*Attorney, Agent, or Firm*—Panitch, Schwarze, Jacobs & Nadel

[57] ABSTRACT

An apparatus is described for locating objects within the body, and particularly concretions situated in body cavities, in three dimensions and for destroying them. The point of departure for this is an electro-acoustic treatment transducer for generating shock waves to be emitted to focus on the object concerned and a B-scanner connected to the treatment transducer to act as a locating transducer for locating the object, the locating transducer being adjustable relative to the treatment transducer co-focally therewith. The design proposed envisages the locating transducer being integrated into the treatment transducer so that the sound fields of both transducers travel the same distances through the same media and it is thus the correct position of the focus relative to the concretion seen in the image which is in fact shown.

13 Claims, 9 Drawing Sheets

APPARATUS FOR LOCATING OBJECTS WITHIN A BODY IN THREE DIMENSIONS AND FOR DESTROYING SUCH OBJECTS

BACKGROUND OF THE INVENTION a) Field of the Invention

This invention relates to an apparatus for locating objects within a body, and particularly concretions situated in body cavities, in three dimensions, and for destroying them, comprising an electro-acoustic treatment transducer for generating shock waves for treatment purposes to be emitted to focus on the object concerned and at least one B-scanner connected to the treatment transducer to act as a locating transducer for locating the object, the locating transducer being adjustable relative to the treatment transducer along a preset path at a constant distance from the shock wave focus (co-focally therewith) so that, depending on the position of the locating transducer, B-scan images can be generated and displayed in different cross-sectional planes and from different viewing angles.

b) Description of the Prior Art

Ultrasonic locating systems employing B-scanners in known apparatus of the present kind (lithotripters) still do not provide the doctor with sufficient information on the size, volume and surface of the concretion to be treated. However, particularly when large gallstones are being treated, it is most important for a satisfactory assessment to be made of the shape and dimensions of the stone, including while the treatment is going on, firstly because an attempt must be made to disintegrate the stone to the maximum possible degree and secondly because there needs to be some way of obtaining exact information on the success achieved with the treatment at the time from the B-scan images shown on a monitor and of documenting this success where required.

It is known (DE 35 43 867 (U.S. Pat. No. 4,832,730) FIGS. 1 and 2) for the locating transducer and the treatment transducer to be arranged on the same axis and for the locating transducer to be adjustable relative to the treatment transducer in rotation on this axis and axially along it. It is true that this allows B-scan images to be generated in various cross-sectional planes, but the concretion cannot be looked at from different viewing angles, hence this solution is still not ideal as far as the information content of the B-scan image is concerned.

A better solution in this respect is one (DE 3543867 C2, (U.S. Pat. No. 4,821,730) FIGS. 3 and 4) in which the locating transducer is externally positioned at the circumference of the treatment transducer and can be adjusted on a circular path concentric with the longitudinal axis of the latter transducer, because when this is the case the concretion intended for destruction can be imaged and studied from different viewing angles as dictated by the position of the locating transducer.

However, even this solution has certain drawbacks relating to accuracy of aim because the sound fields of the two transducers do not travel the same distance through the same media and hence it is not always possible to be sure that the cross-hairs which identify the position of the shock wave focus in the B-scan image, and which may for example be marked on the screen of the monitor belonging to the locating system, do in fact show the correct position of the focus relative to the concretion seen in the image.

Also, it is not possible with the embodiment being discussed for the B-scanner to be arranged at an ideal angle to the axis of the treatment transducer. This is because the angle in question is too large, due to the locating transducer being positioned on the outside of the treatment transducer, thus making it difficult or even impossible, for structural and anatomical reasons, for the sector-shaped scanning plane of the locating transducer to be lined up on the concretion.

Hence it is better for one or more locating transducers trained on the shock wave focus to be arranged on or in the treatment transducer at an acute angle of, for example 15° to the longitudinal axis of the latter (DE 27 22 252 C3; "Piezolith 2300" brochure, issued in September, 1988 by Richard Wolf GmbH, D-7134 Knittlingen, West Germany). However, the solutions of this kind known to date once again suffer from the drawback that the concretion cannot be displayed and studied from different viewing angles.

Hence, the main object of the present invention is substantially to improve the dynamic characteristics, and thus the information content, of the B-scan image generated by the locating transducer or transducers in comparison with known solutions.

SUMMARY OF THE INVENTION

To this end, it is proposed, taking as a point of departure the apparatus described above, that the said path is created by a mechanical guide for the locating transducer, which latter is surrounded by the acoustic shock wave field, and that it extends within the apparatus, i.e. in the treatment transducer, the said treatment transducer taking the form of a self-focussing transducer in the shape of a spherical cup and the path of the locating transducer, i.e. the guide therefore, in it following the active emitting surface of the treatment transducer.

With an apparatus so laid out, the information content relating to the concretion to be treated can be greatly improved because it is then possible to generate a large number of images which show the concretion from different viewing angles. When these images are reproduced, on the screen of a monitor belonging to the locating system for example, there is also the benefit that a pair of cross-hairs which identify the position of the shock wave focus in the B-scan image, and which are marked on the screen of the monitor belonging to the locating system, show the correct position of the focus relative to the concretion seen in the media. This is because the sound fields of both transducers travel the same distances through the same media, thus ruling out different refractions for the wavefronts of the two fields and the imaging errors this could possibly cause. In this way it is possible to achieve an improvement in the accuracy of aim and precision of the treatment, because the sound field of the treatment transducer is subject to the same conditions as that of the locating transducer.

Layouts which are simple in construction and reliable in respect of the locating process are obtained if, when the treatment transducer is seen in plan, the path is a straight line extending perpendicularly or at an angle to the longitudinal axis of the treatment transducer, in which case the path may also intersect the said longitudinal axis.

However, the path may equally well be created by a spherically curved rail-type guide whose center is the shock wave focus, or finally it may be in the form of a circular annulus or a segment of a circular annulus which extends around the longitudinal axis of the treatment transducer.

In a preferred embodiment, the locating transducer may be adjustable along its path by a motor drive, and this may give a further increase in the information content relating to the concretion being treated if the "moving" images obtained in this way from different angles are processed by an additional computer so that the individual images can be shown superimposed on one another by a type of compound-scan process.

The locating transducer may advantageously be associated with the treatment transducer by cutting the latter away in the region of the path and having the locating transducer extend into or through the cutout. At the same time, the locating transducer may be rotatable on its longitudinal axis and also axially displaceable along it, thus making it possible firstly for B-scan images to be obtained in different cross-sectional planes with angular displacements between them equivalent to the angular positions of the locating transducer relative to the longitudinal axis of the treatment transducer, and secondly for the position of the locating transducer to be adjusted to suit the anatomical features of the body of the patient being treated at the time.

Finally, the locating transducer can be made easily interchangeable, for example to allow the apparatus to be adapted to the individual application, by mounting its head to be detachable and interchangeable by means of a plug-in connection.

BRIEF DESCRIPTION OF THE DRAWINGS

In order that the invention may be more readily understood some embodiments thereof will now be described, by way of example, with reference to the accompanying drawings, in which.

DESCRIPTION OF THE PREFERRED EMBODIMENTS

Figure 11:
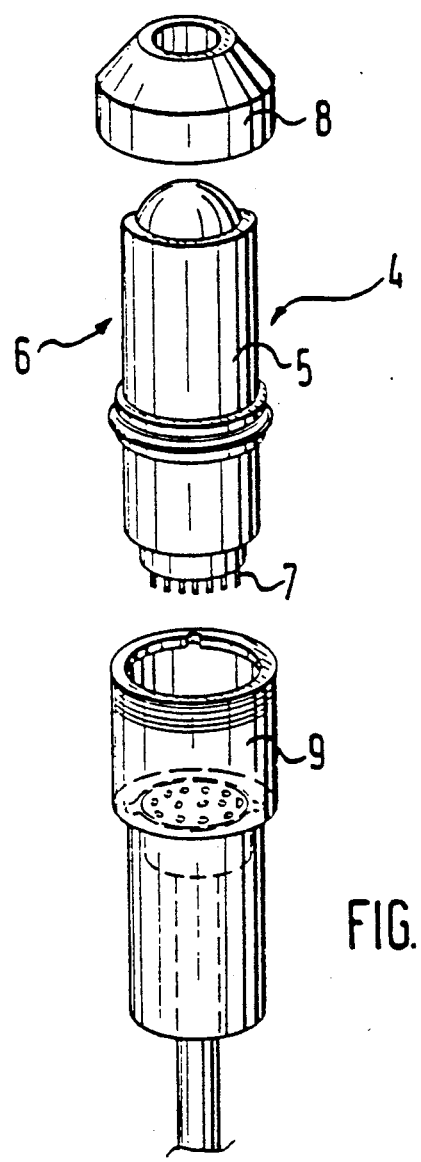
FIG. 11 shows an embodiment of quick-change transducer element.

Referring to the drawings, in all the embodiments shown, the treatment transducer 2 according to the invention is designed as a self-focussing transducer and takes the form of a spherical cup in which individual piezoelectric transducer elements (not shown) are so arranged that their emissions are directed onto a shock wave focus 3. The polar region of the spherical surface of the treatment transducer 2 is free of transducer elements, thus producing over the said region an ultrasound shadow whose envelope is conical in shape. Built into the said polar region is a locating system 4. The locating system comprises a locating transducer 5 which acts as a B-scanner and which, as shown in FIG. 11, may be in the form of a plug-in element 6 provided with a plug-in connector 7. The plug-in element 6 is held in a socket 9 by a screw-on ring 8 with a liquid-tight seal.

Figure 10:
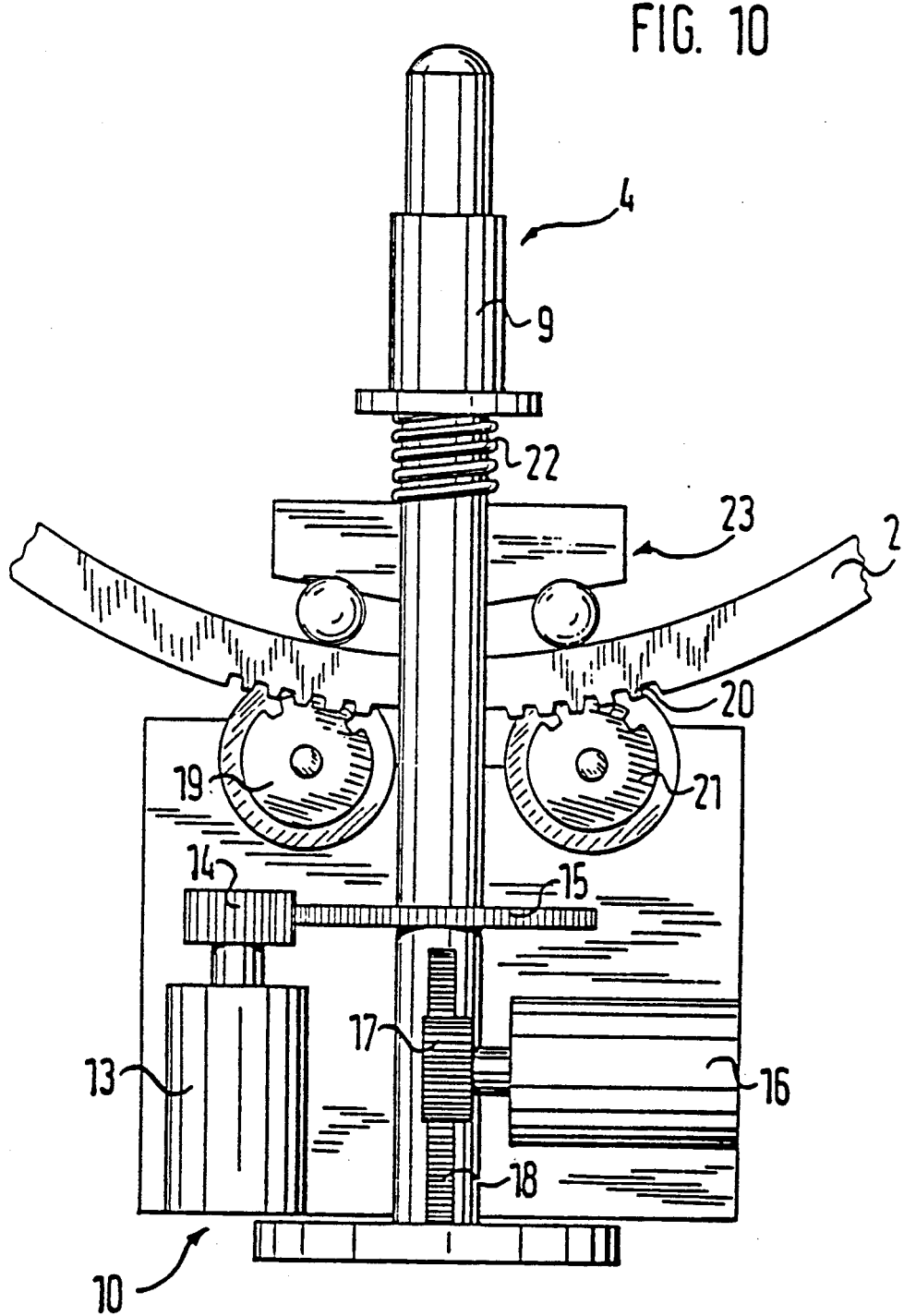
FIG. 10 is an embodiment, shown in diagrammatic form, of a motorized means for producing adjusting movements of the locating transducer.

The socket 9 is part of a carriage 10 which is guided in a cutout 11 in the cup-shaped transducer of the treatment transducer 2. As can be seen in FIG. 10, the carriage 10 is designed as a drive unit which includes drive means for pivoting, rotating and axial displacement relative to the pole of the spherical cup of the treatment transducer 2, and feedback means for whatever positioning sensing system is used. In the embodiment shown diagrammatically in FIG. 10, the drive means for the rotation comprises a controllable motor 13, which rotates the socket 9 and thus the locating transducer 5 on their common axis via gears 14,15. The drive means for the axial displacement likewise comprises a controllable motor 16, which acts on the socket 9 via a pinion 17 and rack 18, the socket being suitably mounted or rather guided in the carriage 10 for this purpose. The pivoting of the locating transducer 5 is performed by a controllable motor (not shown) of which pinions 19, 21 (lantern pinions for example) engages with teeth 20 on the spherical cup of the treatment transducer 2. The curve and configuration of the set of teeth 20 in this case are designed to match the particular shape of the cutout which guides the locating transducer 5.

Figure 7:
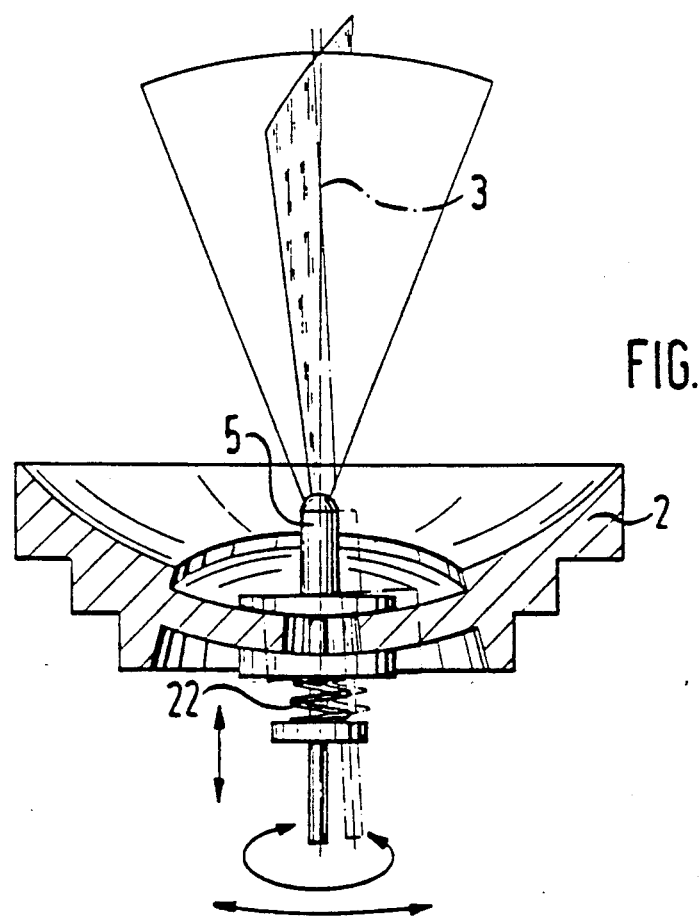
FIG. 7 is a cross-section through a treatment transducer having a spherically guidable locating transducer.
Figure 8:
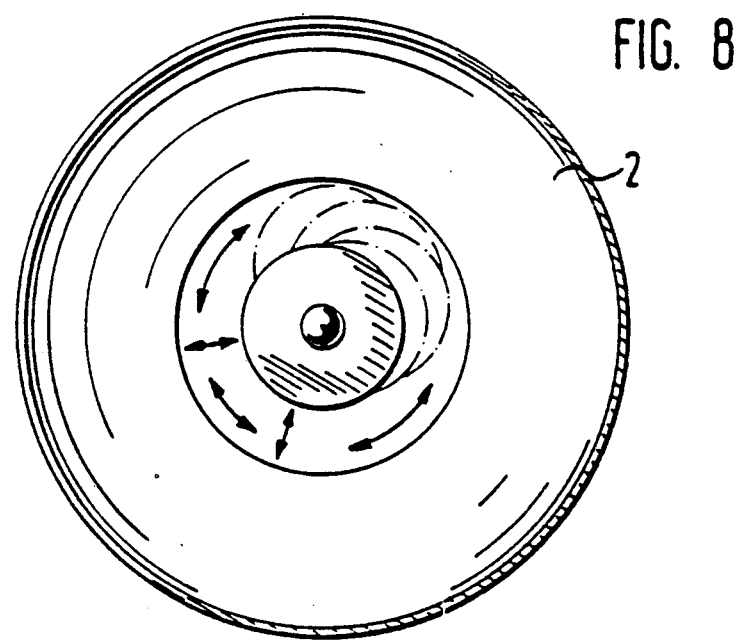
FIG. 8, is a plan view of the treatment transducer seen in FIG. 7.
Figure 9:
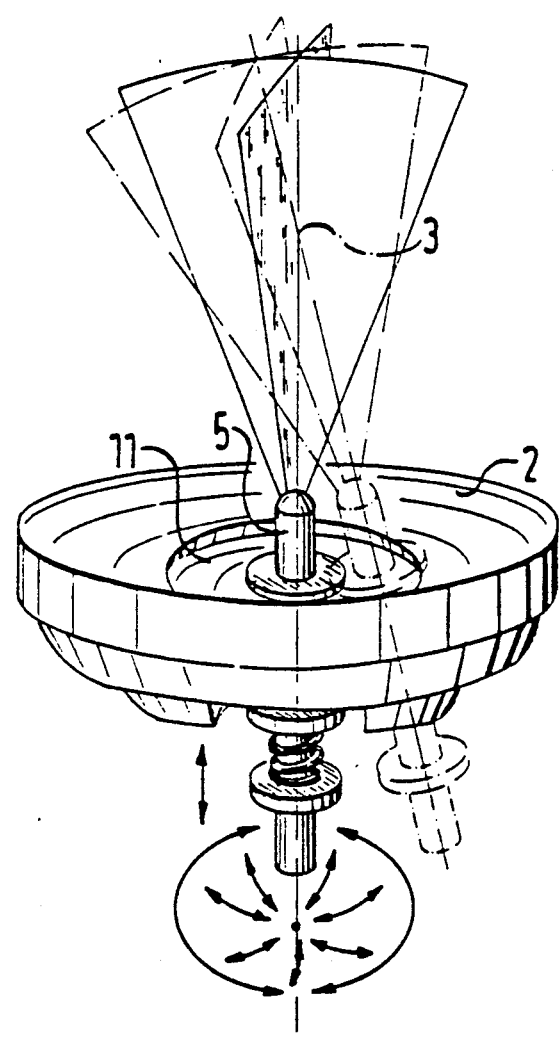
FIG. 9 is an axonometric representation of the treatment transducer as seen in FIGS. 7 and 8.

For a combined movement by the locating transducer 5, as shown in FIGS. 7, 8 and 9, the carriage 10 may be provided (in a manner not shown) with a traveller which is set up to allow the locating transducer 5 to be moved along a meridian of the spherical cup, while the carriage 10 as a whole is displaceable along a line of latitude.

The motors mentioned may be stepping motors which are operated by control signals in pulsed form. The positional feedback in each case may be obtained from a potentiometer (not shown) which acts as a travel sensor.

A spring 22 is responsible for ensuring that the locating transducer 5 is guided without any play, this spring forcing together the carriage 10 which is guided on the outer face of the spherical cup of the treatment transducer 2 and a traveller member 23 positioned on the inner face.

Figure 12:
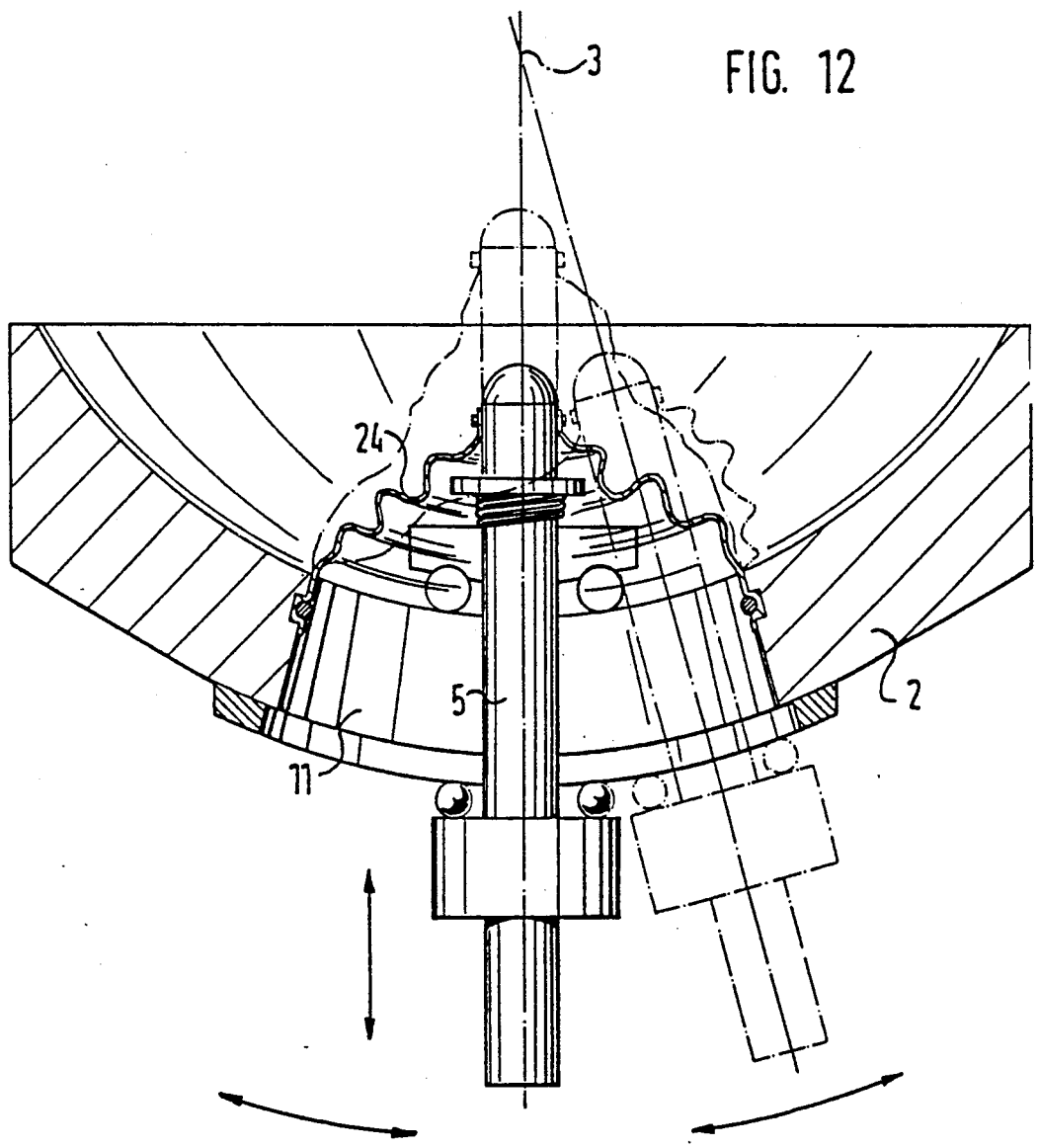
FIG. 12 shows an embodiment of a means for sealing off a locating transducer from the cup of the treatment transducer.

As shown in FIG. 12, the locating transducer 5 is sealed off from the spherical cup of the treatment transducer 2 by means of a gaiter 24 which covers the cutout 11 which forms the track along which the locating transducer 5 moves. The gaiter 24 is fastened to the plug in element 6, or rather to the socket of the locating transducer 5 in such a way that there is a seal even in rotation.

Figure 1:
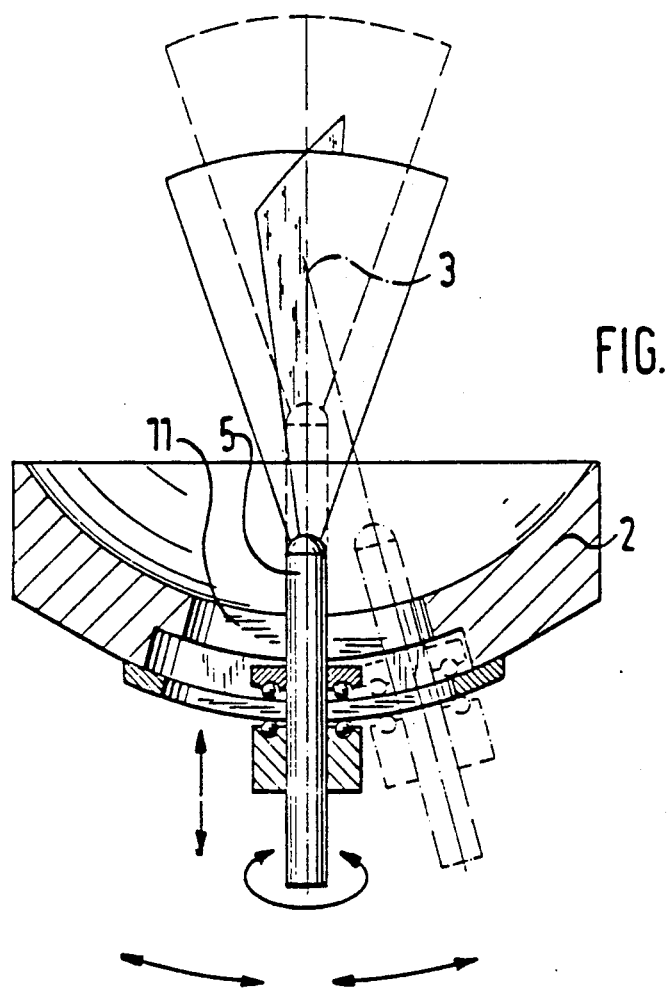
FIG. 1 is a cross-section through a treatment transducer having a locating transducer pivotable therein along a central straight line.
Figure 2:
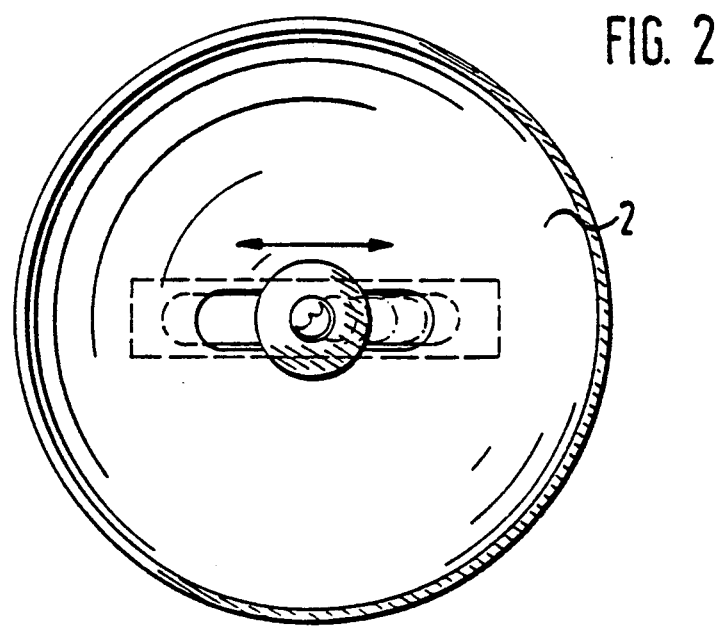
FIG. 2 is a plan view of the treatment transducer shown in FIG. 1.
Figure 3:
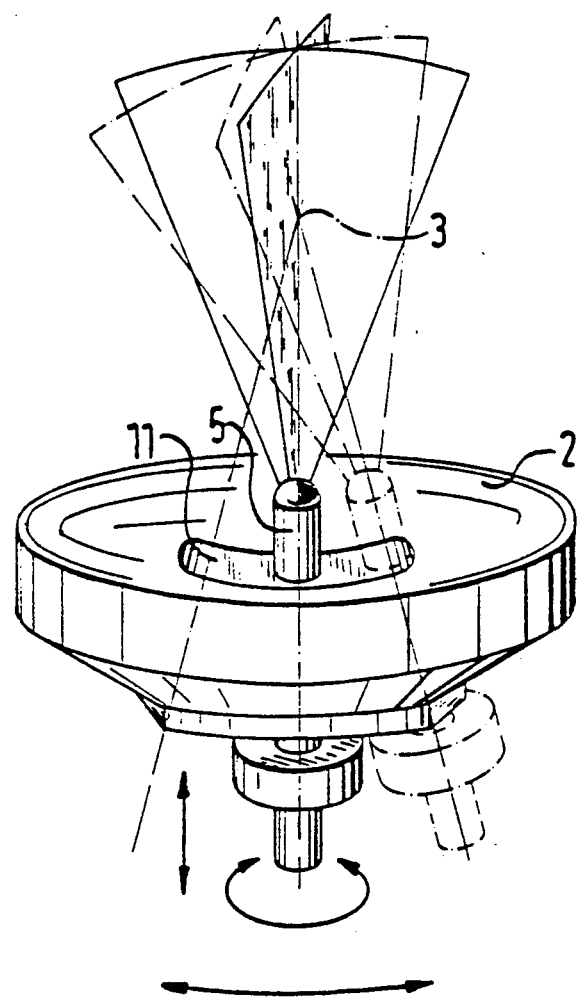
FIG. 3 is an axonometric representation of the treatment transducer shown in FIGS. 1 and 2.
Figure 4:
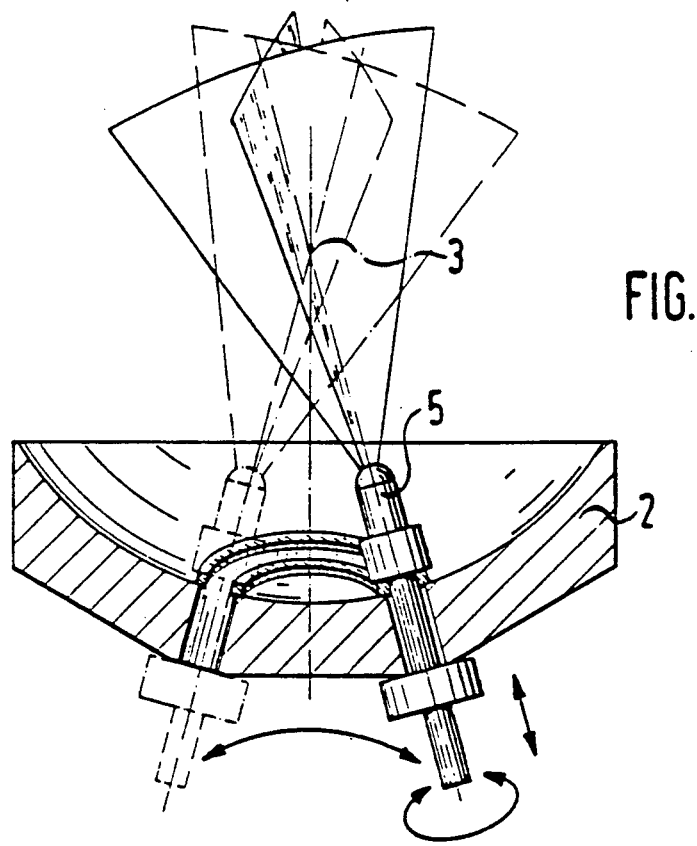
FIG. 4 is a cross-section through a treatment transducer having a locating transducer guidable about the axis of the former, concentrically therewith.
Figure 5:
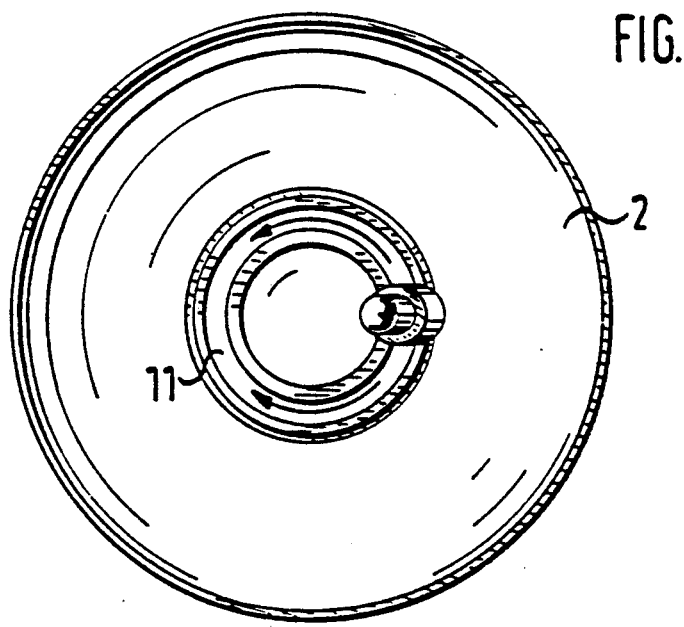
FIG. 5 is a plan view of the treatment transducer seen in FIG. 4.
Figure 6:
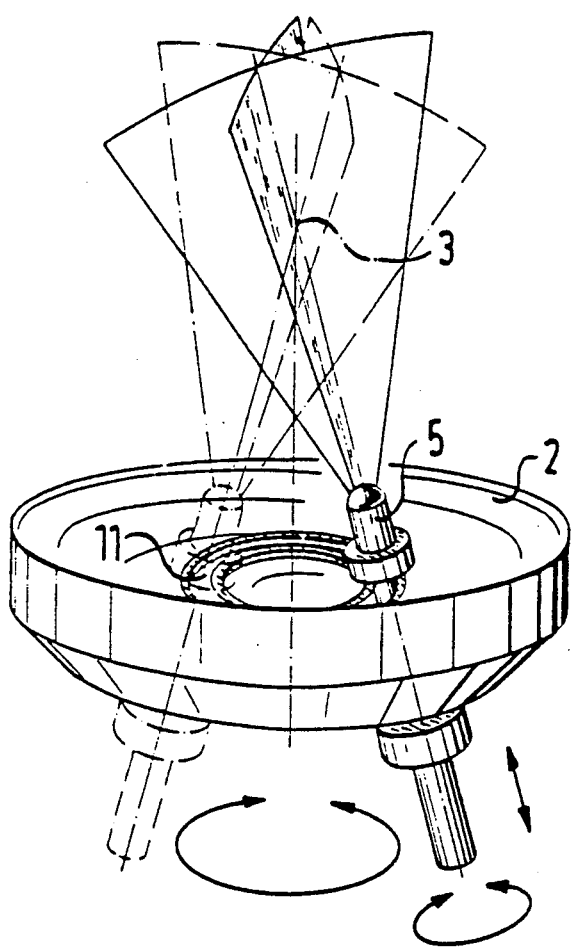
FIG. 6 is an axonometric representation of the treatment transducer seen in FIGS. 4 and 5.

The B-scanner used in the embodiments has a fan-shaped sound field. The locating system 4 constructed as shown in FIGS. 1, 2 and 3 is therefore capable of showing the object which has been located in a multiplicity of cross-sectional planes by rotating the locating transducer 5 on its axis, and of changing the angular position of these planes by means of the pivoting movement. FIG. 3 shows in solid lines the form of the fan-shaped sound fields when the locating transducer 5 is turned through 90°, while in broken lines it shows the fields when the locating transducer 5 is in a pivoted position. In the case of the apparatus shown in FIGS. 4, 5 and 6, the object which has been located can both be displayed in a multiplicity of cross-sectional planes and be viewed from various positions but at a constant angle. The apparatus shown in FIG. 9 combines the types of display possible with the pieces of apparatus shown in FIGS. 3 and 6.

We claim:

1. Apparatus for locating objects within a body in three dimensions and for destroying said objects, said apparatus comprising electro-acoustic treatment transducer means for generating shock waves to be emitted to focus on one said object, said treatment transducer means having a longitudinal axis on which said focus is positioned, locating transducer means for locating said object comprising at least one B-scanner and being connected to said treatment transducer means, means for adjusting the position of said locating transducer means relative to said longitudinal axis of said treatment transducer means along a path at a constant distance from and co-focal with said shock wave focus, whereby at different positions of said locating transducer means B-scan images are generated and displayed in different cross-sectional planes and from different viewing angles, and mechanical guide means for creating said path for said locating transducer means which is surrounded by an acoustic shock wave field and extends within said treatment transducer means.

2. Apparatus according to claim 1 wherein said treatment transducer means is in the shape of a spherical cup having an active emitting surface, and said path of said locating transducer means follows said active emitting surface.

3. Apparatus according to claim 1 wherein said path extends transverse to the longitudinal axis of said treatment transducer means.

4. Apparatus according to claim 3 wherein said path, when viewed along said longitudinal axis, appears to follow a straight line.

5. Apparatus according to claim 3 wherein said path intersects said longitudinal axis.

6. Apparatus according to claim 1 wherein said guide means comprises a spherically curved rail-type guide whose center of curvature is said shock wave focus.

7. Apparatus according to claim 1 wherein said path is in the form of a circular annulus which extends around said longitudinal axis.

8. Apparatus according to claim 1 wherein said path is in the form of a segment of a circular annulus which extends partly around said longitudinal axis.

9. Apparatus according to clam 1 wherein said adjusting means comprises motor driven means.

10. Apparatus according to claim 1 wherein said path comprises a cutout in said treatment transducer means and said locating transducer means extends into said cutout.

11. Apparatus according to claim 1 wherein said locating transducer means has a longitudinal axis and is rotatable on its longitudinal axis.

12. Apparatus according to claim 1 wherein said locating transducer means is axially adjustable.

13. Apparatus according to claim 1 wherein said locating transducer means has a head which is detachable and interchangeable.

* * * * *